US007081635B2

(12) United States Patent
Baumann

(10) Patent No.: US 7,081,635 B2
(45) Date of Patent: Jul. 25, 2006

(54) HIGH ACTIVITY, SPATIALLY DISTRIBUTED RADIATION SOURCE FOR ACCURATELY SIMULATING SEMICONDUCTOR DEVICE RADIATION ENVIRONMENTS

(75) Inventor: Robert Christopher Baumann, Dallas, TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 11/087,288

(22) Filed: Mar. 22, 2005

(65) Prior Publication Data

US 2005/0186326 A1 Aug. 25, 2005

Related U.S. Application Data

(62) Division of application No. 10/421,063, filed on Apr. 23, 2003, now Pat. No. 6,914,447.

(51) Int. Cl.
*A61M 36/14* (2006.01)

(52) U.S. Cl. ..................... 250/493.11; 427/5; 324/765; 324/752; 324/158.1; 324/824

(58) Field of Classification Search ..................... None
See application file for complete search history.

(56) References Cited

U.S. PATENT DOCUMENTS 5,395,783 A 3/1995 Baumann et al.
5,523,597 A 6/1996 Baumann et al.
6,239,479 B1 5/2001 Hwang et al.
6,348,356 B1 2/2002 Shabde et al.
6,365,042 B1 4/2002 Sorensen et al.
6,410,414 B1 6/2002 Lee
6,436,737 B1 8/2002 Malladi
6,483,134 B1 11/2002 Weatherford et al.
6,484,289 B1 11/2002 Hsu
2003/0030444 A1 2/2003 Kogawa et al.

OTHER PUBLICATIONS

"The Impact of Technology Scaling on Soft Error Rate Performance and Limits to the Efficacy of Error Correction", Institute of Electrical and Electronics Engineers (IEEE) International Electron Devices Meeting (IEDM), Robert Baumann, Dec. 2002, 4 pages.

*Primary Examiner*—Nikita Wells
*Assistant Examiner*—Zia R. Hashmi
(74) *Attorney, Agent, or Firm*—Rose Alyssa Keagy; W. James Brady, III; Frederick J. Telecky, Jr.

(57) ABSTRACT

The present invention pertains to radiation sources that mimic radiation environment(s) encountered by packaged semiconductor devices. The sources are suitable for use in test systems operative to test for soft error and/or failure rates in devices sensitive to such radiation. The radiation is highly active to exacerbate soft error rates and thereby accelerate testing and reduce test times. The sources are also relatively uniformly distributed within a medium to simulate the direction(s) and energy spectra of radiation that would actually be encountered by semiconductor devices in device operation.

7 Claims, 8 Drawing Sheets

HIGH ACTIVITY, SPATIALLY DISTRIBUTED RADIATION SOURCE FOR ACCURATELY SIMULATING SEMICONDUCTOR DEVICE RADIATION ENVIRONMENTS

This is a division of application Ser. No. 10/421,063, filed Apr. 23, 2003 now U.S. Pat. No. 6,914,447.

FIELD OF INVENTION

The present invention relates generally to semiconductor technologies and more particularly to radiation sources that mimic radiation environment(s) encountered by packaged semiconductor devices to facilitate accelerated soft error or other radiation effects testing.

BACKGROUND OF THE INVENTION

Several trends presently exist in the semiconductor device fabrication industry and in the electronics industry. Devices are continually getting smaller, faster and requiring less power, while simultaneously being able to support a greater number of increasingly sophisticated applications. One reason for these trends is that there is an ever increasing demand for small, portable and multifunctional electronic devices. For example, cellular phones, personal computing devices, and personal sound systems are devices which are in great demand in the consumer market. These devices rely on one or more small batteries, which are generally rechargeable, as a power source and also require an ever increasing storage capacity to store data, such as digital audio, digital video, contact information, database data and the like.

To achieve these and other ends, a continuing trend in the semiconductor manufacturing industry is toward producing smaller and faster transistor devices, which consume less power and provide more memory density. Integrated circuits (ICs) are thus continually designed with a greater number of layers and with reduced feature sizes and distances between features (e.g., at sub micron levels). This can include the width and spacing of interconnecting lines, the spacing and diameter of contact holes, and the surface geometry such as corners and edges of various features. The scaling-down of integrated circuit dimensions can facilitate faster circuit performance, more memory and can lead to higher effective yield in IC fabrication by providing more circuits on a die and/or more die per semiconductor wafer.

Semiconductor based products (e.g., DSP's, microprocessors) can include and be utilized on a variety of different items including one or more different types of memory, such as static random access memory (SRAM), dynamic random access memory (DRAM) and/or embedded memory, as well as logic such as latches, flip-flops and/or combinatorial logic that interconnects memory to cache(s). Respective types of memory generally include thousands or millions of memory cells, adapted to individually store and provide access to data. A typical memory cell stores a single binary piece of information referred to as a bit. The cells are commonly organized into multiple cell units such as bytes which generally comprise eight cells, and words that may include sixteen or more such cells, usually configured in multiples of eight. Storage of data in such memory device architectures is performed by writing to a particular set of memory cells, sometimes referred to as programming the cells. Retrieval of data from the cells is accomplished in a read operation. In addition to programming and read operations, groups of cells in a memory device may be erased.

The erase, program, and read operations are commonly performed by application of appropriate voltages to certain terminals or nodes of the cells. In an erase or program operation the voltages are applied so as to cause a charge to be stored in the memory cells. In a read operation, appropriate voltages are applied so as to cause a current to flow in the cells, wherein the amount of such current is indicative of the value of the data stored in the respective cells. The memory devices include appropriate circuitry to sense the resulting cell currents in order to determine the data stored therein, which may then be provided to data bus terminals for access by other devices in a system in which the memory device is employed.

As the dimensions and operating voltages of electronic devices are reduced to satisfy the ever-increasing demand for higher density and lower power, their sensitivity to radiation increases dramatically. Radiation can, directly or indirectly, induce localized ionization events capable of upsetting internal data states. While the upset causes a data error, the circuit itself is undamaged; thus this type of event is called a “soft” error and the rate at which these events occur is called the soft error rate (SER). It has been established that SER in semiconductor devices is induced by three different types of radiation; alpha particles, high-energy neutrons from cosmic radiation, and/or the interaction of cosmic ray thermal neutrons and 10B in devices containing borophosphosilicate glass.

SUMMARY OF THE INVENTION

The following presents a simplified summary of the invention in order to provide a basic understanding of some aspects of the invention. This summary is not an extensive overview of the invention. It is intended neither to identify key or critical elements of the invention nor to delineate the scope of the invention. Rather, its purpose is merely to present one or more concepts of the invention in a simplified form as a prelude to the more detailed description that is presented later.

One or more aspects of the present invention pertain to radiation sources that mimic radiation environment(s) encountered by packaged semiconductor devices. The sources are highly active to exacerbate soft error rates and thereby accelerate testing and reduce test times. The sources are also spatially distributed within a medium to simulate the spectra of radiation emitted from device packaging.

According to one or more aspects of the present invention, a method of forming a radiation source is disclosed. The radiation source is suitable for use in a test system operative to test for soft error or failure rates in one or more semiconductor devices where the devices may fail as a result of exposure to test radiation from the test radiation source, and more particularly where respective charge sensitive nodes of the devices, which experience ever decreasing capacitances and voltages as device scaling occurs, are adversely affected by exposure to the test radiation, wherein the test radiation mimics radiation that the devices would actually encounter in practice. The method includes substantially uniformly distributing one or more radioisotopes into a matrix material to a specific depth from the surface, wherein the radioisotopes act as emission sites and emit the test radiation.

According to one or more other aspects of the present invention, substantially uniformly distributing one or more radioisotopes into a matrix material includes depositing a layer of the one or more radioisotopes onto a top surface of the matrix material and subjecting the matrix material and the layer of radioisotopes to a high temperature anneal to cause at least some of the radioisotopes to move down toward a bottom surface of the matrix material.

In accordance with one or more other aspects of the present invention, the one or more radioisotopes have a relatively short half life such that the devices experience an increased exposure to the test radiation as compared to the amount of the radiation that the devices would actually receive in device operation, and such that the devices exhibit an enhanced soft error rate so that testing time is thereby reduced.

In accordance with yet one or more other aspects of the present invention, the test radiation is emitted from the bottom surface of the matrix material and wherein the substantially uniform distribution of the radioisotopes allows the radiation to encounter the one or more semiconductor devices being tested at a wide variety of angles and with a variety of different energies similar to what would actually be encountered in practice.

According to one or more other aspects of the present invention, a radiation source is disclosed. The radiation source is suitable for use in a test system operative to test for soft error or failure rates in one or more semiconductor devices where the devices may fail as a result of exposure to test radiation from the test radiation source, and more particularly where respective charge sensitive nodes of the devices, which experience ever decreasing capacitances and voltages as device scaling occurs, are adversely affected by exposure to the test radiation, wherein the test radiation mimics radiation that the devices would actually encounter in device operation. The test radiation source includes a matrix material and one or more radioisotopes substantially uniformly distributed within the matrix material, wherein the radioisotopes act as emission sites and emit the test radiation.

To the accomplishment of the foregoing and related ends, the following description and annexed drawings set forth in detail certain illustrative aspects and implementations of the invention. These are indicative of but a few of the various ways in which one or more aspects of the present invention may be employed. Other aspects, advantages and novel features of the invention will become apparent from the following detailed description of the invention when considered in conjunction with the annexed drawings.

DETAILED DESCRIPTION OF THE INVENTION

Figure 1:
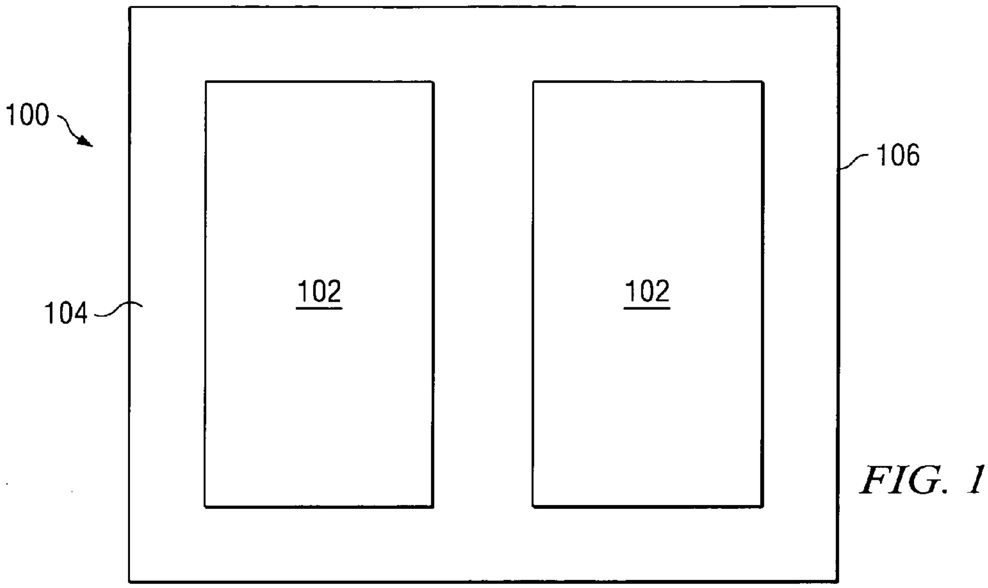
FIG. 1 is a plan view of an exemplary memory device.

One or more aspects of the present invention are described with reference to the drawings, wherein like reference numerals are generally utilized to refer to like elements throughout, and wherein the various structures are not necessarily drawn to scale. In the following description, for purposes of explanation, numerous specific details are set forth in order to provide a thorough understanding of one or more aspects of the present invention. It may be evident, however, that one or more aspects of the present invention may be practiced with a lesser degree of these specific details. In other instances, structures and devices are shown in block diagram form in order to facilitate describing one or more aspects of the present invention.

One or more aspects of the present invention relate generally to semiconductor devices that include and are utilized in, among other things, memory, such as static random access memory (SRAM) and/or dynamic random access memory (DRAM), and logic devices, such as latches, flip-flops and/or other combinatorial logic that, among other things, interconnects memory and cache(s). Such semiconductor devices and/or elements or components thereof possess charge-sensitive interconnections or nodes that can be affected by exposure to radiation which can cause the devices to experience increased soft error rates. The sensitivity of these interconnections or nodes to the radiation is continually increasing as a result of scaling whereby critical voltages and capacitances are continually being reduced.

More particularly, one or more aspects of the present invention pertain to test systems and associated methodologies that are utilized to characterize or develop soft error or failure rate data for semiconductor devices. Even more particularly, one or more aspects of the present invention pertain to radiation sources that mimic radiation environment(s) encountered by packaged semiconductor devices. The sources are highly active to exacerbate soft error rates and thereby accelerate testing and reduce test times. The sources are also spatially distributed within a medium to simulate the spectra of radiation emitted from device packaging.

By way of example, it will be appreciated that electronic memory devices include a plurality of individual cells that are organized into individually addressable units or groups such as bytes or words, which are accessed for read, program, or erase operations through address decoding circuitry, whereby such operations may be performed on the cells within a specific byte or word. The memory devices include appropriate decoding and group selection circuitry to address such bytes or words, as well as circuitry to provide voltages to the cells being operated on in order to achieve the desired operation.

In a random access memory (RAM), for example, an individual binary data state (e.g., a bit) is stored in a volatile memory cell, wherein a number of such cells are grouped together into arrays of columns and rows accessible in random fashion along bitlines and wordlines, respectively, wherein each cell is associated with a unique wordline and bitline pair. Address decoder control circuits identify one or more cells to be accessed in a particular memory operation for reading or writing, wherein the memory cells are typically accessed in groups of bytes or words (e.g., generally a multiple of 8 cells arranged along a common wordline). Thus, by specifying an address, a RAM is able to access a single byte or word in an array of many cells, so as to read or write data from or into that addressed memory cell group.

Two major classes of random access memories include dynamic (e.g., DRAM) and static (e.g., SRAM) devices. For a DRAM device, data is stored in a capacitor, where an access transistor gated by a wordline selectively couples the capacitor to a bit line. DRAMs are relatively simple, and typically occupy less area than SRAMs. However, DRAMs require periodic refreshing of the stored data, because the charge stored in the cell capacitors tends to dissipate. Accordingly DRAMs need to be refreshed periodically in order to preserve the content of the memory. SRAM devices, on the other hand, do not need to be refreshed. SRAM cells typically include several transistors configured as a flip-flop having two stable states, representative of two binary data states. Since the SRAM cells include several transistors, however, SRAM cells occupy more area than do DRAM cells. However, SRAM cells operate relatively quickly and do not require refreshing and the associated logic circuitry for refresh operations.

Other types of memory also exist, such as Flash and EEPROM, which overcome a disadvantage of SRAM and DRAM devices, namely volatility. SRAM and DRAM devices are said to be volatile as they lose data stored therein when power for such devices is removed. For instance, the charge stored in DRAM cell capacitors dissipates after power has been removed, and the voltage used to preserve the flip-flop data states in SRAM cells drops to zero, by which the flip-flop loses its data. Flash and EEPROM devices are said to be non-volatile as they do not lose data stored therein when power is removed. However, these types of memory devices have operational limitations on the number of write cycles. For instance, Flash memory devices generally have life spans from 100K to 10 MEG write operations.

Table 1 illustrates some exemplary differences between different types of memory.

TABLE 1

| Property | SRAM | Flash | DRAM | FRAM (Demo) |
|---|---|---|---|---|
| Voltage | >0.5 V | Read >0.5 V Write (12 V) (±6 V) | >1 V | 3.3 V |
| Special Transistors | NO | YES (High Voltage) | YES (Low Leakage) | NO |
| Write Time | <10 ns | 100 ms | <30 ns | 60 ns |
| Write Endurance | $>10^{15}$ | $<10^{5}$ | $>10^{15}$ | $>10^{13}$ |
| Read Time (single/multi bit) | <10 ns | <30 ns | <30 ns/<2 ns | 60 ns |
| Read Endurance | $>10^{15}$ | $>10^{15}$ | $>10^{15}$ | $>10^{13}$ |
| Added Mask for embedded | 0 | ~6–8 | ~6–8 | ~3 |
| Cell Size (F~metal pitch/2) | ~80 $F^2$ | ~8 $F^2$ | ~8 $F^2$ | ~18 $F^2$ |
| Architecture | NDRO | NDRO | DRO | DRO |
| Non volatile | NO | YES | NO | YES |
| Storage | I | Q | Q | P |

Turning now to FIG. 1, a plan view of an exemplary memory device 100 is depicted. The memory device 100 may comprise one or more core regions 102 and a peripheral portion 104 on a single substrate 106. The core regions 102 typically comprise at least one M×N array of individually addressable, substantially identical memory cells. The peripheral portion 104 typically includes, among other things, logic elements, such as gates, registers, flip-flops and latches that are effective to, among other things, form input/output (I/O) circuitry and/or other circuitry that facilitates selectively addressing the individual cells (e.g., decoders for connecting source, gate and drain regions of selected cells to predetermined voltages or impedances to produce designated operations of the cell, such as programming, reading and/or erasing).

Figure 2:
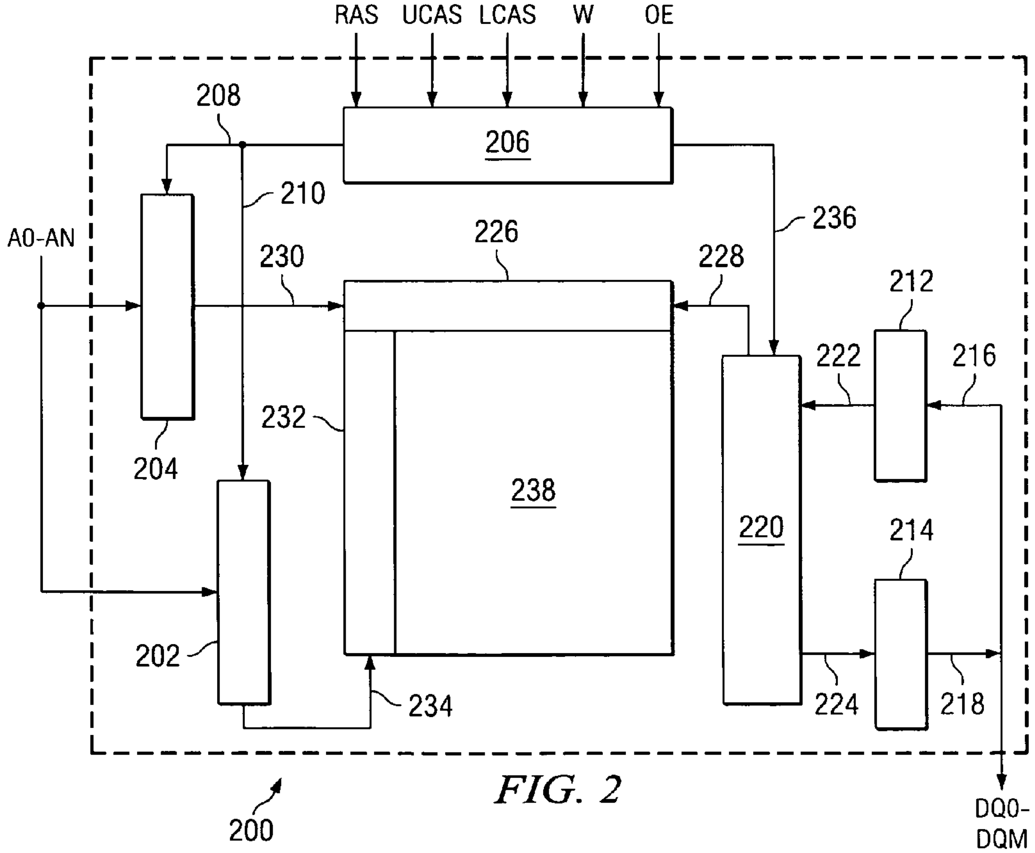
FIG. 2 illustrates an exemplary DRAM memory device in schematic block diagram form.

By way of further example, an example of a DRAM memory device 200 is illustrated in somewhat greater detail in schematic block diagram form in FIG. 2. It will be appreciated, however, that application of one or more aspects of the present invention is in no way meant to be limited to DRAM or specific components thereof, but that the instant discussion is merely provided for exemplary purposes. The memory device 200 receives address signals A0–AN, N being an integer, in row address buffers 202 and column address buffers 204. The address signals become latched in the address buffers by use of control signals, for example, RAS (Row Address Strobe), UCAS (Upper Column Address Strobe), and LCAS (Lower Column Address Strobe) received in timing and control block 206. Desired timing and control signals are then carried from control block 206 to buffers 202, 204 via leads 208, 210.

Data signals DQ0–DQM, M being an integer, are carried in parallel to a data in register 212 and a data out register 214 via leads 216, 218, respectively. A plurality of data signals (e.g., eighteen) pass in parallel from the data in register 212 to the I/O buffer 220 via lead 222. Similarly, a plurality of data signals (e.g., eighteen) pass in parallel from the I/O buffer 220 to the data out register 214 via lead 224. A plurality of data signals (e.g., thirty six) also pass in parallel from the I/O buffer 220 to one or more column decoders 226 via lead 228. The column decoders 226 also receive a plurality of address signals (e.g., eight) in parallel from column address buffers 204 via lead 230. Row decoders 232 similarly receive a plurality of address signals (e.g., twelve)

in parallel from row address buffers 202 via lead 234. The I/O buffer 220 receives timing and/or control signals from the timing and control block 206 via lead 236. Control signals W (Write) and OE (Output Enable) connect to timing and control block 206 to indicate and control the writing and reading of data signals from the overall array 238.

It will be appreciated that column decoders 226 and row decoders 232 can address individual memory cells contained within the overall array 238, and that the overall array 238 can include, for example, 18,874,368 (18M) memory cells, where each memory cell is capable of containing one data bit that can, for example, be configured in 1,048,576 words by 18 bits per word (1M.times.18). It will be further appreciated that the overall array 238 can contain a plurality of array parts (e.g., seventy two), where respective array parts contain a plurality of memory cells (e.g., 256K). The overall array 238 can also be separated into two halves where the row decoders 232 separate the two halves and where a plurality of array paths (e.g., thirty six) are then located on either side of the row decoders 232.

It will be appreciated that parts of the device, such as the memory cells and non-memory peripheral or glue logic (e.g., 202, 204, 206, 212, 214, 220 as well as other elements which may or may not be shown in the example illustrated) can include charge-sensitive interconnections or nodes which may be affected by radiation, such as by being induced with additional charge, which can cause failures or soft errors. The errors are referred to as soft errors because, while data may be corrupted, these elements themselves remain unaffected.

Figure 3:
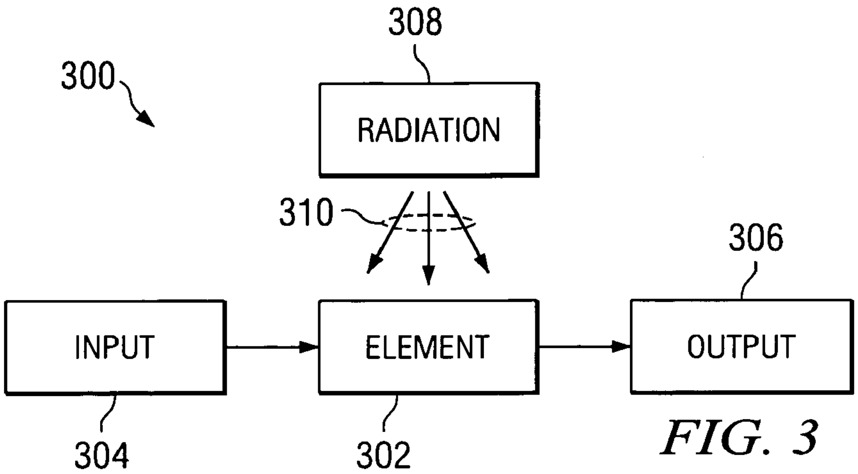
FIG. 3 illustrates in schematic block diagram form a test system suitable for testing for and/or characterizing soft error or failure rates in semiconductor devices according to one or more aspects of the present invention.

Turning to FIG. 3, a system 300 is depicted in schematic block diagram form that facilitates testing for and/or characterizing soft error or failure rates in semiconductor products such as, for example, static random access memory (SRAM). A test element 302, an input 304, an output 306 and a source of radiation 308 are included in the exemplary system shown. The test element 302 includes the item or device to be tested, and may comprise a plurality of elements of the type of element to be tested (e.g., flip-flop$_A$, flip-flop$_B$, flip-flop$_C$, etc.). The elements may be connected in series as a string of elements (e.g., on the order of a thousand or more elements) to magnify the occurrence of soft errors and thereby accelerate the test time. It will be appreciated that while an arrangement of a string of elements is described, any suitable configuration of elements can be implemented according to one or more aspects of the present invention. For example, the elements to be tested can be arranged in parallel and/or as an XY array, such as the memory elements described with respect to FIGS. 1 and 2, but with a plurality of latches, flip-flops, combinatorial elements, or other types of elements to be tested taking the place of the memory cells within the array. Additionally, should multiple strings of elements be utilized to concurrently test multiple types of elements, the strings may or may not include equal numbers of respective elements. It will be appreciated, however, that it may easier to readout data from chains having equal lengths as the data output will likely be synchronized.

The radiation source 308 is located adjacent to the item and is operative to selectively expose the item to one or more types of radiation 310 for a particular period of time and/or at a particular intensity to mimic actual packaged conditions. Such radiation can include, for example, alpha particles. Upon interaction with a semiconductor device, the radiation can cause a disruption in an electrical signal or can corrupt information stored by localized nodes within the device. Such a failure may be referred to as a soft error because while data is corrupted, the circuit itself remains unaffected.

Data is fed into the element 302 (or string of elements) by the input 304 and comes out at the output 306. By way of example, the input 304 can include a data source and a clock operative to clock data into the element or string of elements (e.g., in a known pattern such as all 1's, all 0's, a pattern of repeating 1's and 0's, or the like). The radiation source 308 is controllable so that the element(s) 308 can be selectively exposed to the radiation 310 (e.g., for a particular period of time). The element(s) can, for example, be exposed to the radiation 310 as data is clocked into the element(s) and can remain exposed to the radiation as the data passes through the element(s) and subsequently exits the element(s) 308. Alternatively, the element(s) can be filled with data prior to being exposed to the radiation 310 and then be exposed to the radiation 310 for a particular period of time, after which the data is read out of the element(s) at the output 306 while no longer being exposed to the radiation 310. The occurrence of failures or soft errors can be determined, for example, by comparing input data to data output. For example, if a series of 1's were clocked into the element(s), then the number of 0's output would be indicative of the rate of failures for the particular type of element being tested given the particular conditions (e.g., radiation time, type, intensity) under which the test was performed.

Failure rates in a particular time frame can then be obtained for the respective types of elements being tested since the radiation exposure time, type and intensity are known, and the number of elements that fail during this exposure time period can be been determined. This can be utilized to compute what an actual failure rate would be for the respective elements when the elements are implemented in the field.

Charge generated from radiation on junctions or nodes within semiconductor devices is sometimes referred to as collected charge. If the collected charge is grater than the charge of the data state stored in a particular node, the critical charge, then a soft error is likely to occur. Some junctions within the elements are driven to have particular charges, while others are floating nodes and/or are very weakly driven. If more charge exists on a node or if a node is being driven to provide additional charge to compensate for radiation induced charge, then the probability of a soft error occurring is significantly reduced. Thus, an element with a relatively high critical charge is difficult to upset and does not readily exhibit soft errors. As a corollary, an element that is sensitive to the external radiation and that has a relatively low critical charge is easily upset and can exhibit soft errors when exposed to even mild spurious charges.

Nevertheless, there is not necessarily a one-to-one correspondence between critical charge and soft error, and thus two elements can have similar critical charges yet have different soft error rates. Accordingly, while one may anticipate different elements to have similar soft error rates, where those elements have similar critical charges, the elements may in fact have different soft error rates. Thus, developing failure rate characterization data facilitates determining what the soft error rates will actually be for particular elements or logic cells, regardless of the critical charges of those elements. This mitigates ambiguity and/or unreliability present in resulting semiconductor devices, and allows for an estimate of soft error performance.

A significant source of ionizing radiation in semiconductor devices is the result of naturally occurring radioactive particles found in material(s) utilized to fabricate semiconductor devices, such as DRAMs, SRAMs, A/D converters, and so forth, which rely on electrical charge on a capacitive node for storage of a digital signal, and thus which can be sensitive to events which transport unintended charge to the node. Uranium and Thorium impurities are found in semiconductor fabrication materials in trace amounts and are radioactive and emit alpha particles as they decay. The naturally occurring isotopes are U238 and Th232. Even in relatively pure materials with Uranium/Thorium impurity levels below parts-per-billion, the alpha emission can be high enough to cause a soft error in a semiconductor product, which can, for example, affect memory cell state retention.

Additionally, semiconductor device packaging can include, among other things, plastic and ceramic packages. Plastic packaging surrounds, among other things, a semiconductor die and its bond wires and lead frame with a thickness of about 2 mm, for example. Plastic packaging can, for example, include 27% novalac epoxy, 70% inert filler, 2% flame retardant, 1% colorant, plus accelerator, curing agent, and mold-release agent, where the filler can include powdered quartz. However, quartz, for example, can include natural uranium (U) and thorium (Th) impurities whose radioactive decay gives rise to alpha particles which can generate bursts of electrical charges that can migrate and upset stored signal charge on a node. Ceramic packages can, for example, have a body of 90% alumina plus 10% glass with lids of gold-plated kovar, a glass sealer, and air within the package cavity. All of these components may similarly have alpha-emitting radioactive impurities, such as radon in cavity air, for example.

Referring now to FIGS. 4–8, a discussion is provided with regard to packaging of semiconductor devices and the interconnection of components therein as well as to potentially disruptive radioisotopes given off thereby. Wire bond and flip-chip type connections are discussed as these are two common techniques for electronically coupling semiconductor circuitry within integrated circuit packaging materials.

Figure 4:
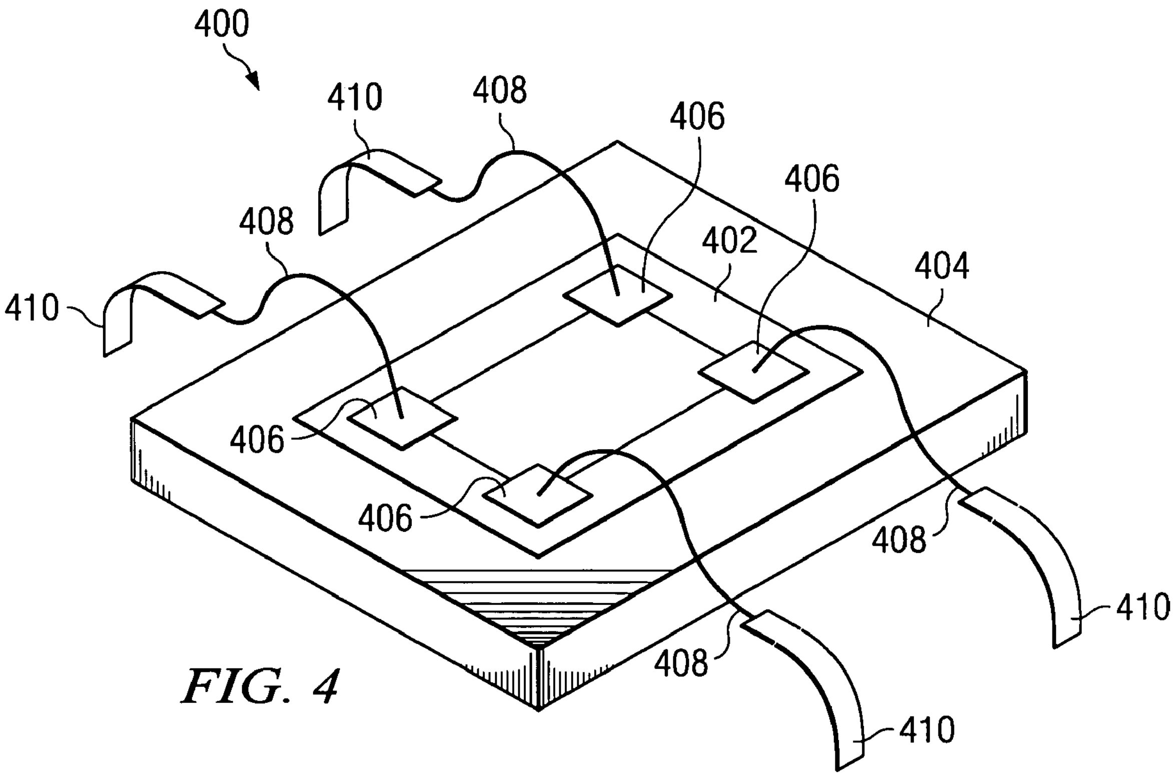
FIG. 4 illustrates in perspective view a wire bond type connection of a semiconductor device that is not yet shrouded within a packaging material.

In FIG. 4 an exemplary wire bond type connection is depicted on a device 400 that is yet to be enclosed within a packaging material. In the example shown, a semiconductor die 402 is situated on a substrate 404, for example, a leadframe pad. The die 402 may be situated so that its active circuitry is facing up and that its inactive backside is facing down toward an upper surface of the substrate 404. A plurality of electrically conductive bond pads 406 reside on the die 402 and are associated with the circuitry thereon. The bond pads 406 facilitate electrical connection between the die 402 and the outside world. More particularly, the bond pads 406 provide a means by which conductive wires 408 connect the circuitry of the die 402 to pins 410 which are operative to facilitate coupling of the device to a printed circuit board or other substrate. It will be appreciated that while four bond pads 406, four conductive wires 408 and four pins 410 are depicted in the example illustrated, a different number of these items may be comprised within semiconductor devices and that such elements need not be present in equal numbers.

Figure 5:
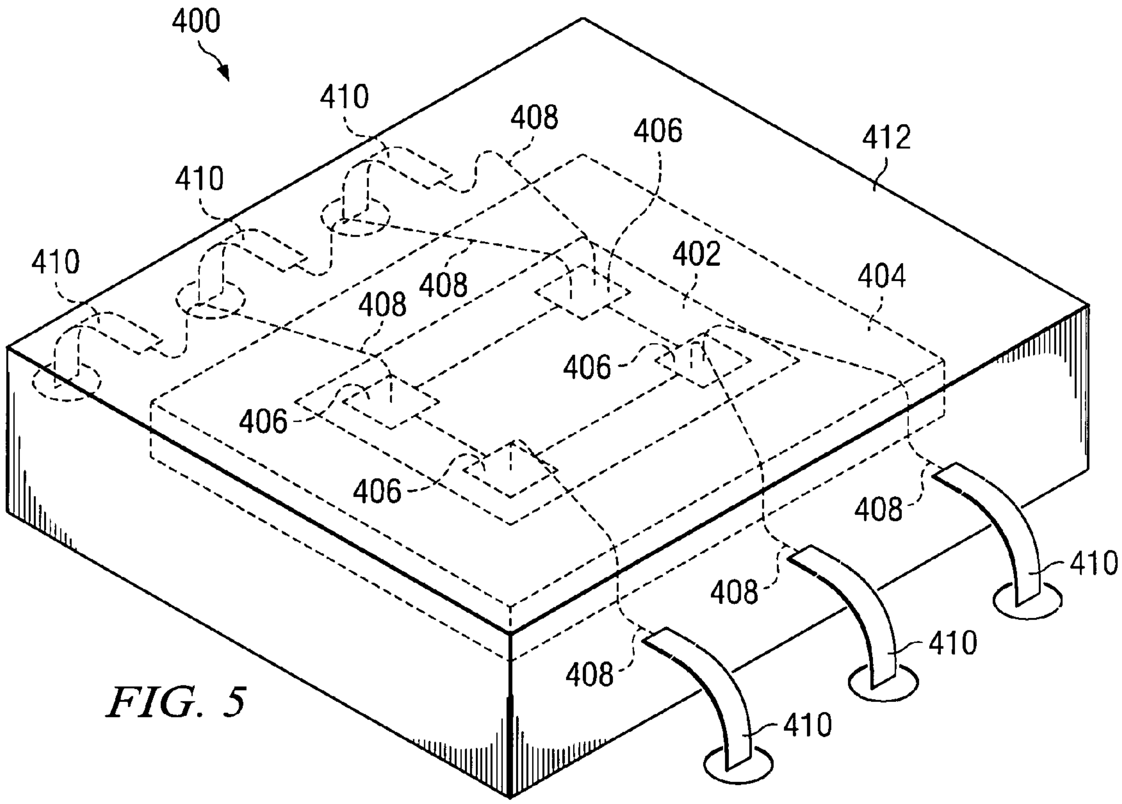
FIG. 5 illustrates in perspective view an exemplary semiconductor device such as that depicted in FIG. 4, but encapsulated within a packaging material.

FIG. 5 is a representation of an exemplary device 400 such as that depicted in FIG. 4 encapsulated within a packaging material 412 or package body. The packaging material 412 serves to protect the semiconductor die 402 and other components and/or materials contained therein from external contaminants. The packaging material 412 also serves to steady and/or fix components within the device and to protect interconnections within the device (e.g., as the device may be jostled about during use). It will be appreciated that the packaging material 412 may be formed from a variety of substances, either alone or in combination, such as plastic, epoxy, alumina, glass-ceramic and/or one or more polymers, for example.

It will be further appreciated that additional substances may be included within the device, such as those, for example, that may be utilized to make up appropriate metal inter-connection layers and/or solder balls, which may be utilized to interconnect the device to a printed circuit board or other substrate and/or to interconnect different components within the device (e.g., one or more wires 408 to one or more bond pads 406).

Additional materials may similarly be utilized to attach the die 402 to the substrate 404, including, for example, epoxy, polyamides, metal filled polymers, ceramic filled polymers, diamond filled polymers, silver glass, copper, aluminum, various alloys, plastics and/or other suitable materials, either alone or in combination. An optional heat sink can also be attached utilizing, for example, a high thermal conductivity adhesive that can include, for example, an epoxy or polyurethane, a thermal grease and/or other thermoplastic materials having melting points of less than 200 degrees Celsius, for example.

Figure 6:
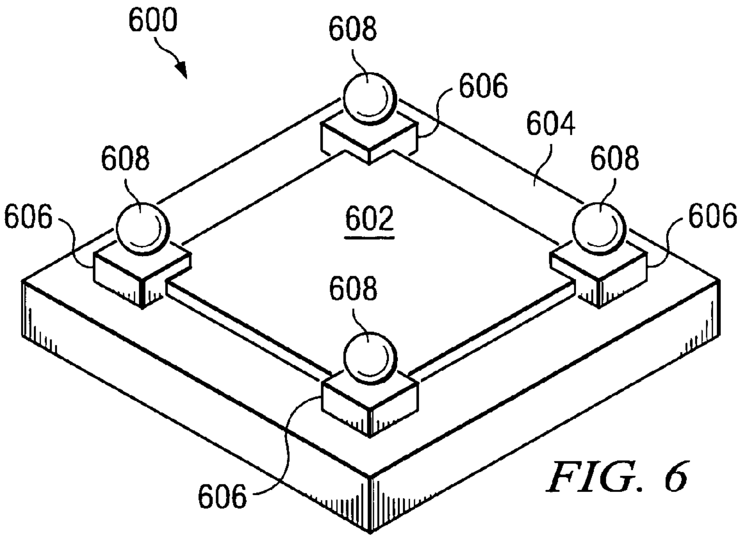
FIG. 6 illustrates in perspective view a flip-chip type sub-assembly of a semiconductor device not yet shrouded within a packaging material.
Figure 7:
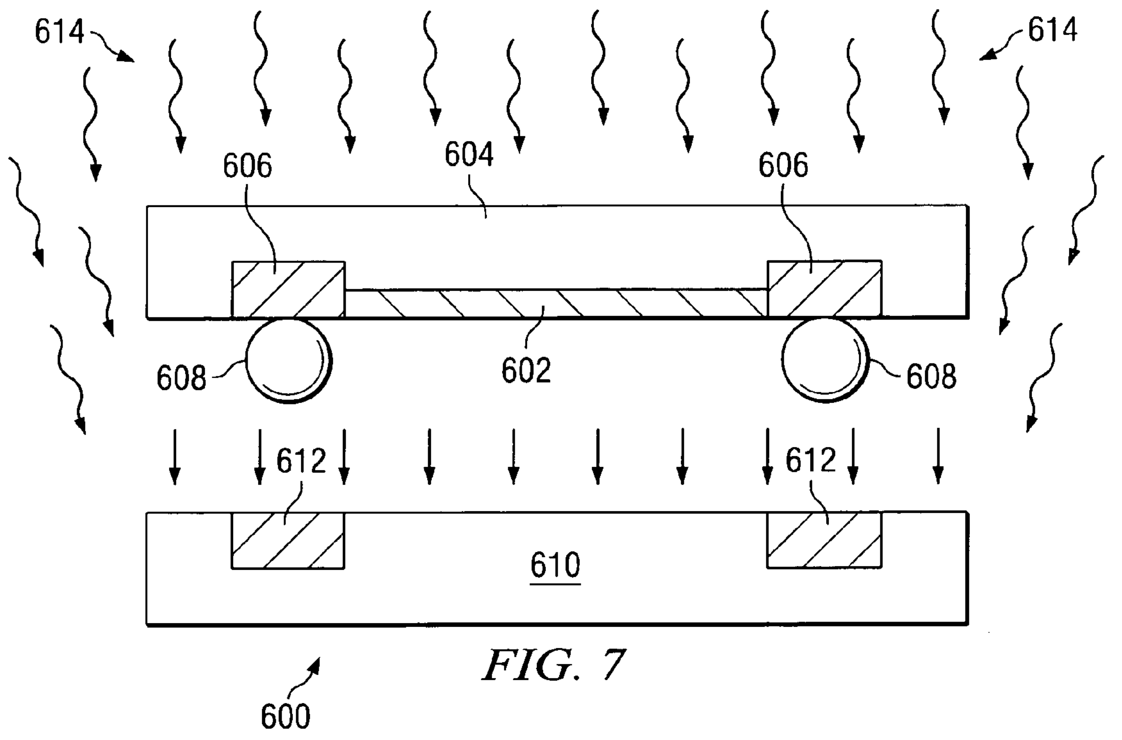
FIG. 7 is a cut away side view illustrating a coupling of a flip-chip sub-assembly, such as that depicted in FIG. 6, to another component via the use of solder balls.
Figure 8:
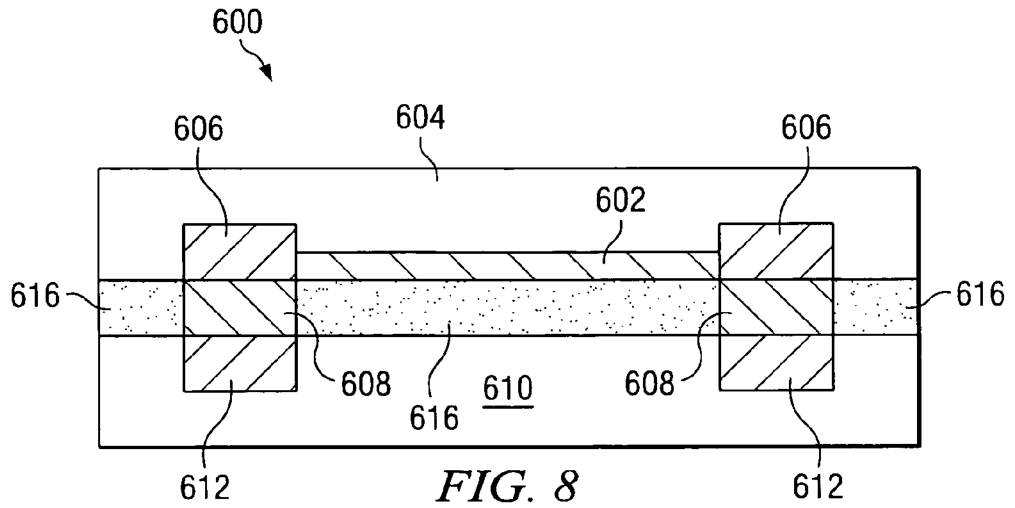
FIG. 8 is a cut away side view illustrating an operative interconnection between bond pads of a flip-chip sub-assembly, such as that depicted in FIG. 6, and contact pads of another component via the use of solder balls.

Turning to FIGS. 6–8, a flip-chip assembly 600 is illustrated for a discussion of a second technique of preparing an integrated circuit package. In FIG. 6, the flip-chip assembly 600 includes a semiconductor chip or die 602 situated on a carrier or mounting material 604. A plurality of electrically conductive bond pads 606 are operatively coupled to the die 602 and circuitry thereon. Respective bumps 608 are included on the bond pads 606 to facilitate electrical and mechanical coupling of the die 602 to other components.

FIG. 7 illustrates the coupling of the flip-chip assembly 600 to another component, such as to a substrate 610 operatively coupled to active circuitry (not shown). More particularly, the die 602 is inverted or flipped such that the bumps 608 are aligned with respective contact pads 612 operatively coupled to active circuitry supported on the substrate 610. Energy 614 is then applied to facilitate coupling the die 602 to the contact pads 612 via the bumps 608. More particularly, the bumps 608 generally comprise solder and/or a conductive polymer which can be cured or reflowed through the application of heat energy 614 such that a resultant electromechanical interconnection is formed between the bond and contact pads 606, 612.

FIG. 8 illustrates the operative interconnection between the bond pads 606 and the contact pads 612 via the melted or re-flowed solder bumps 608. It will be appreciated that a filler material 616 may be introduced in a space or gap that may exist between the die 602 and the substrate. This material 616 serves to reinforce the solder joints 608 which may experience stress as a result of different coefficients of thermal expansion, different operating temperatures and/or different operating and mechanical properties of the materials utilized within the device. The reinforcing filler material 616 generally acts as an insulator and can be fashioned from any of a variety of materials, such as aluminum oxide, silicon oxide and/or polymeric materials, for example. It will be appreciated that the substrate can similarly include any of a number of materials, alone or in combination, such as ceramic, silicone and/or glass, for example. It will be further appreciated that one or more of the materials in the device can give off radiation that can affect charge sensitive nodes. For materials that are in close proximity to the die and/or circuitry thereon, such as solder and/or packaging materials, this may be true even where the radiation is given off in very small amounts (e.g., as from Uranium/Thorium impurity level below parts per billion). Such radiation may have an energy range of about of about 0 to 10 MeV, for example.

Figure 9:
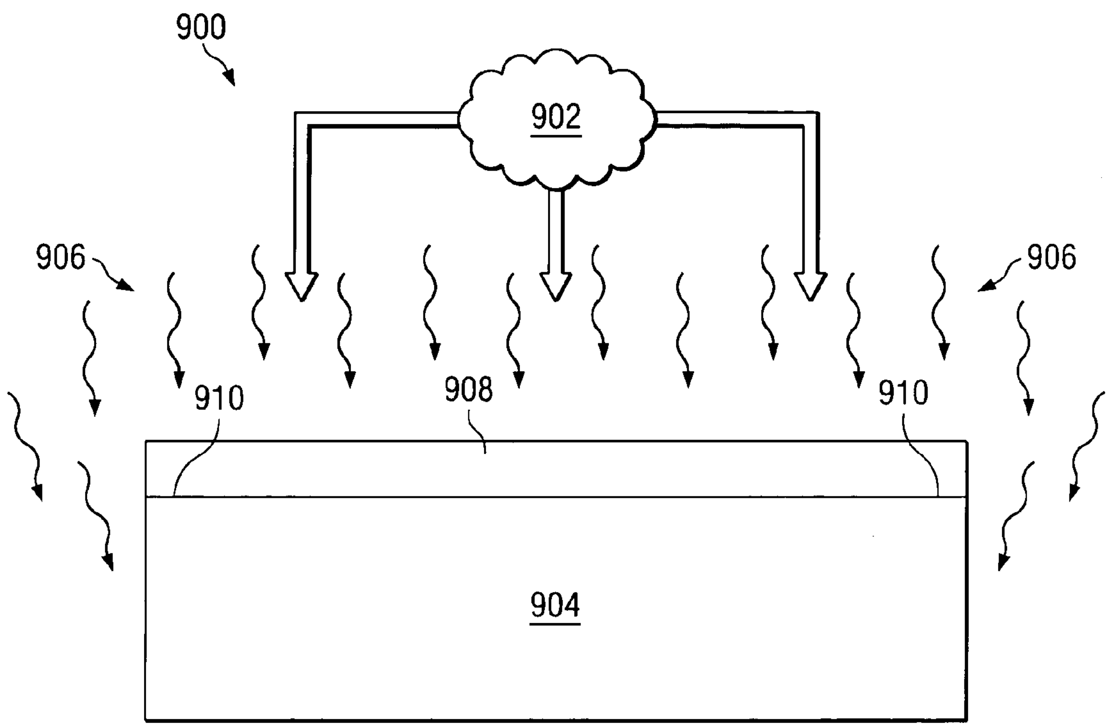
FIG. 9 is a cut away side view illustrating fashioning of a radiation source according to one or more aspects of the present invention.

Turning to FIG. 9, fashioning of a radiation source 900 according to one or more aspects of the present invention is depicted. The radiation source 900 is designed to mimic radiation that a semiconductor device would be exposed to in practice by packaging and/or other materials. However, the radiation is significantly more active than that which would be encountered in device operation, and thus increases the rate of soft errors and reduces test times. To form the radiation source 900, one or more radioisotopic materials 902 are added to an encapsulation matrix 904 under particular processing conditions 906.

The radioisotopic materials utilized are chosen such that their emission energies are similar to that of corruptive alpha or other particles. The radioisotopes are also highly active (e.g., have a short half life) so that the elements that are exposed to the radiation experience an increased dosage of the radiation to expedite the testing process. The radioisotope exposure may, for example, have a flux that is several orders of magnitude more intense than that to which a device would be subjected under normal operating conditions. Error rates experienced by the test devices are thereby enhanced and the testing time is reduced.

The radioisotopes are also imparted to the matrix so as to be relatively uniformly distributed therein. This allows the radiation particles to bombard the elements being tested at a wide variety of different angles and with a variety of different energies similar to what would actually be encountered in practice. The different energy levels are achieved, at least in part, because the particles lose energy as they travel through the matrix. In particular, the more material the particles have to traverse to escape the matrix, the less energy they have when they leave the matrix. These different angles and energy levels more accurately mimic the randomness and spectra of radiation that the device would actually be exposed to in device operation.

It will be appreciated that the matrix 904 can include any of a number of suitable materials, alone or in combination, such as metal, semiconductor and/or ceramic matrix materials comprising, respectively, platinum, stainless steel, silicon and/or alumina, for example. Additionally, radioisotropic materials 902 can include any one or more isotopes that have alpha emissions similar to that of impurities within packaging and/or other materials which are the source of radiation in real devices. By way of example, one or more types of thorium (e.g., Th-228) can be utilized to simulate alpha emissions from mold compounds used to encapsulate many integrated circuits (ICs). Th-228 is a good candidate since it is part of the natural thorium decay chain and also has a very high relative activity. In particular, Th-228 can be utilized to simulate, for example, alphas emitted from thorium and uranium impurities in a silica filler emitted over a broad range of energies (e.g., from about 0–10 MeV). A type of americium (e.g., Am-241) can also be utilized, for example, to simulate emissions from flip-chip solder bumps. Am-241 is a good candidate since it has a relatively high activity and can be utilized to simulate alphas emitted from impurities in lead. In particular, Am-241 simulates, for example, alphas emitted from polonium (e.g., Po-210) that have an emission spectrum of about 0–5.3 MeV. Americium with emissions in the range of about 5–5.5 MeV uniformly distributed within the matrix could, for example, be utilized to simulate this range as isotopes buried deep within the matrix would lose a significant portion of their energy while exiting the matrix. Such sources have a high intensity so that relatively short experiments (e.g., well under a few days) can be done to gather sufficient amounts of test data.

It will be appreciated that the distribution of the radioisotopic materials 902 within the matrix 904 can be accomplished in any of a number of different fashions, including, for example, thermal diffusion, implantation and/or mixing of the isotope with a liquid or powdered matrix which is then solidified by curing, annealing and/or some other process. In one example, a layer 908 of the radioisotopes is deposited onto a top surface 910 of the matrix 904 and then subjected to a very high temperature anneal process 906 to substantially uniformly diffuse the layer 908 into the matrix material 904.

Figure 10:
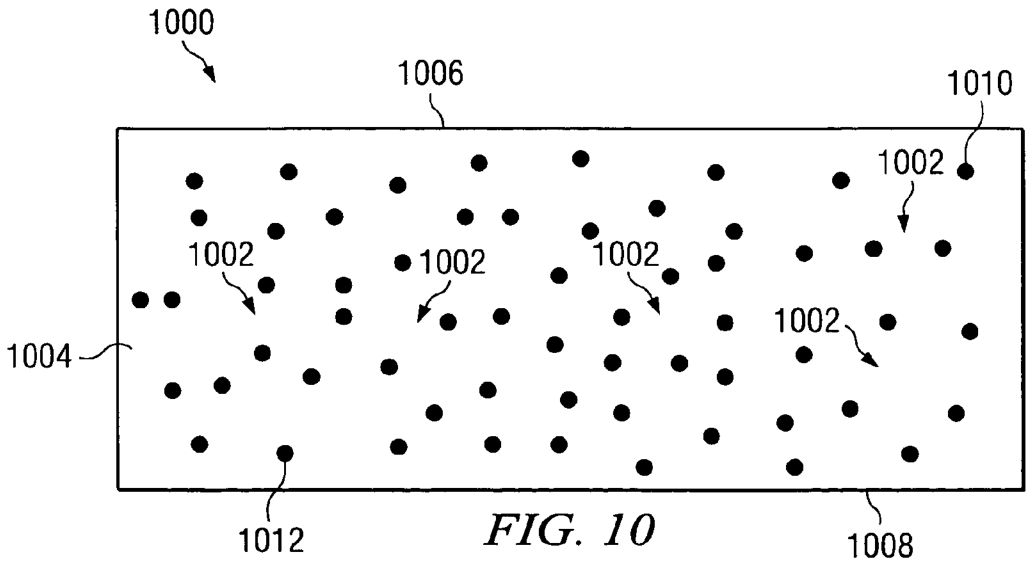
FIG. 10 is a cut away side view depicting a radiation source fashioned in accordance with one or more aspects of the present invention.

FIG. 10 depicts a cross-sectional view of a radiation source 1000 fashioned in accordance with one or more aspects of the present invention. The radiation source 1000 is suitable for use in a system (e.g., such as that depicted in FIG. 3) adapted to test for and/or characterize soft error or failure rates in semiconductor components where the components are affected by different types of radiation, and where the sensitivity of the devices to the respective types of radiation is dependent upon and/or a function of, among other things, device scaling whereby capacitance and/or voltages, among other things, of charge sensitive nodes are reduced.

The radiation source 1000 includes one or more radioisotopic materials 1002 (e.g., atoms) distributed substantially uniformly within a matrix material 1004. The radioisotopic materials 1002 serve as emission sites and are operative to emit radiation that mimics that to which the device being tested would actually encounter under normal operating conditions (e.g., due to packaging and/or other materials such as solder balls adjacent to the semiconductor device). The radioisotopic materials 1002 can be imparted into the matrix material 1004 in any suitable manner, and can comprise any suitable materials, either alone or in combination, to mimic radiation that the semiconductor device would actually encounter.

A layer of the radioisotopic materials can, for example, be deposited onto a top surface 1006 of the matrix material 1004 and then be subjected to a very high temperature anneal process to substantially uniformly diffuse the layer down into the matrix material 1004 toward a bottom surface 1008 of the matrix material 1004. Additionally, the radioisotopic materials 1004 can comprise, for example, thorium (e.g., Th-228) and americium (e.g., Am-241) to simulate alphas emitted from packaging and/or soldering materials over a broad range of energy levels (e.g., from about 0–10 MeV). The radiation source 1000 reflects the reality that impurities are randomly distributed throughout packaging and that ions bombard chips from many different angles and at many different energy levels. The radioisotopic materials 1004 are also highly active (e.g., have a short half life) to accelerate testing by increasing soft error rates.

Figure 11:
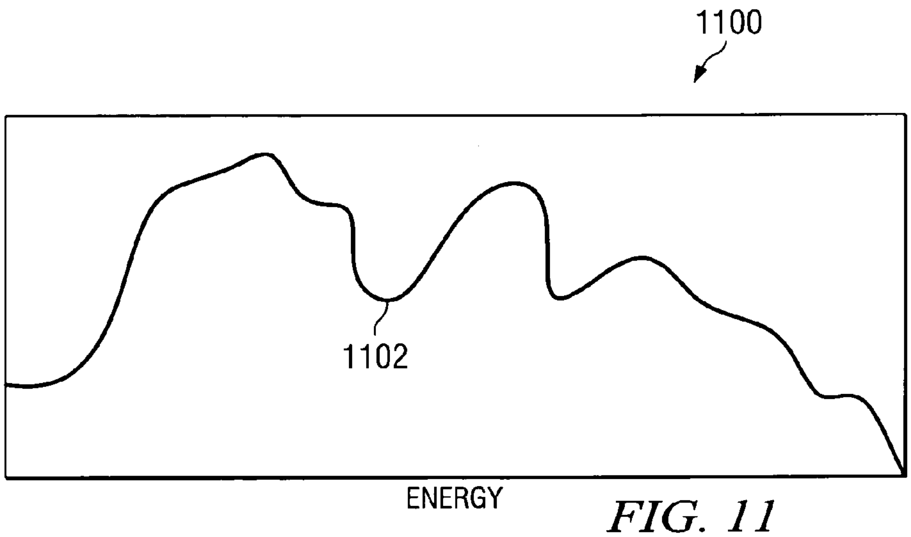
FIG. 11 is a graphical depiction of an exemplary particle energy spectrum generated from a radiation source fashioned in accordance with one or more aspects of the present invention.

FIG. 11 graphically depicts an exemplary particle energy spectrum 1100 generated from a radiation source fashioned in accordance with one or more aspects of the present invention. An exemplary curve 1102 depicted within the graphical illustration is somewhat smooth and gradual as one or more different types of isotopes having respective initial energy levels are substantially uniformly scattered throughout a matrix material and travel different distances thereby losing different amounts of energy as they matriculate through and depart the matrix material.

By way of example, should the curve 1102 in FIG. 11 be derived from the exemplary radiation source 1000 illustrated in FIG. 10, the different radioisotopic sources 1002 lose different amounts of energy as they travel different distances through the matrix material 1004 to exit out the bottom 1008 of the matrix material 1004 before encountering a test device (not shown). For example, an alpha particle emitted from a particular emission site 1010 (e.g., of Am-241) may have an original energy level of about 5 MeV, but may exit out the bottom 1008 of the matrix material 1004 at an energy level of nearly 0 MeV as it has to travel through virtually the entire thickness of matrix material 1004 before exiting the material, losing energy along the way. A different alpha particle emitted from a different emission site 1012 (e.g., of Th-228), on the other hand, may have an initial energy of about 10 MeV, and may exit out the bottom 1008 of the matrix material 1004 at nearly the same energy level as it travels only a slight distance through the matrix material before escaping, and therefore loses very little energy. It will be appreciated that that amount of energy lost by particles, such as alpha particles, is a function of, among other things, the type and/or density of the matrix material. In particular, more energy is lost by particles traveling through mediums that have a higher density, while less energy is lost by particles traveling through mediums that have a lower density.

Figure 12:
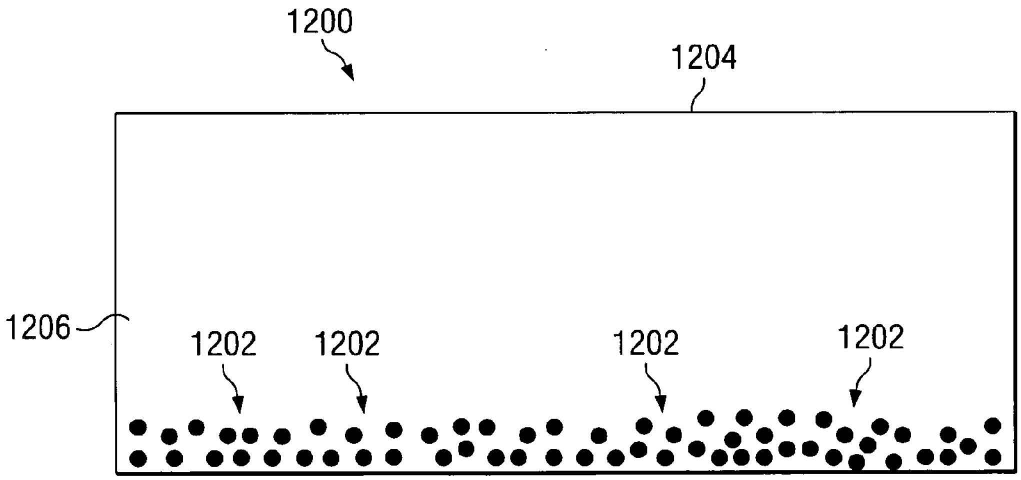
FIG. 12 is a cut away side view depicting a radiation source wherein a plurality of emission sites are located near a bottom surface of a layer of matrix material that encapsulates the sites.

FIG. 12 illustrates a cross sectional side view of a radiation source 1200 wherein a plurality of emission sites 1202 (e.g., atoms) are located near a bottom surface 1204 of a layer of matrix material 1206 that encapsulates the sites 1202. Particles emitted from the sites 1202, such as alpha particles, travel a very short distance (e.g., on the order of about a micron or less) before exiting out the bottom surface 1204 of the material 1206 to encounter a test device. As such, the particles lose very little energy and impact the test device with respective energy levels very similar to their original energy levels (e.g., between about 4–9 MeV depending upon the types of type of materials utilized, such Am-241 and/or Th-228, for example).

Figure 13:
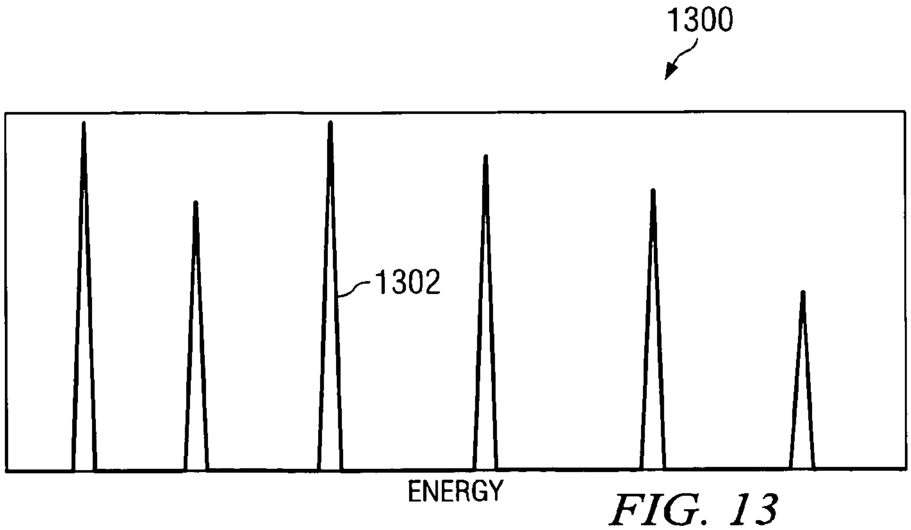
FIG. 13 is a graphical depiction of an exemplary alpha particle energy spectrum from a radiation source, such as that depicted in FIG. 12.

FIG. 13 is a graphical depiction of an exemplary alpha particle energy spectrum 1300 from a radiation source, such as that depicted in FIG. 12, wherein radioisotope atoms are configured in a tight distribution near a surface 1204 of a radiation source. Multiple emissions 1302 are illustrated within the graphical illustration having very well defined and extremely tight energy distributions. The curves correspond to the respective energy levels of different types of radioisotope sources 1202 included near the surface 1204 of the matrix material 1206 (e.g., Am-241, Th-228). Particles, such as alpha particles, emitted from these sources are emitted at specific energy levels that act like fingerprints for the particular types of isotope sources.

Nevertheless, while the discreet curves 1302 in FIG. 13 may be useful to identify different types of isotopes in the radiation source, this is a less than accurate approximation of alpha spectra actually encountered by semiconductor devices in practice (e.g., from packaging and/or other materials such as solder balls located near semiconductor circuitry). The broad spectrum depicted in FIG. 11 is a much more accurate representation of radiation from actual sources since real sources do not produce mono-energetic radiation having very specific energy peaks in their spectra.

Figure 14:
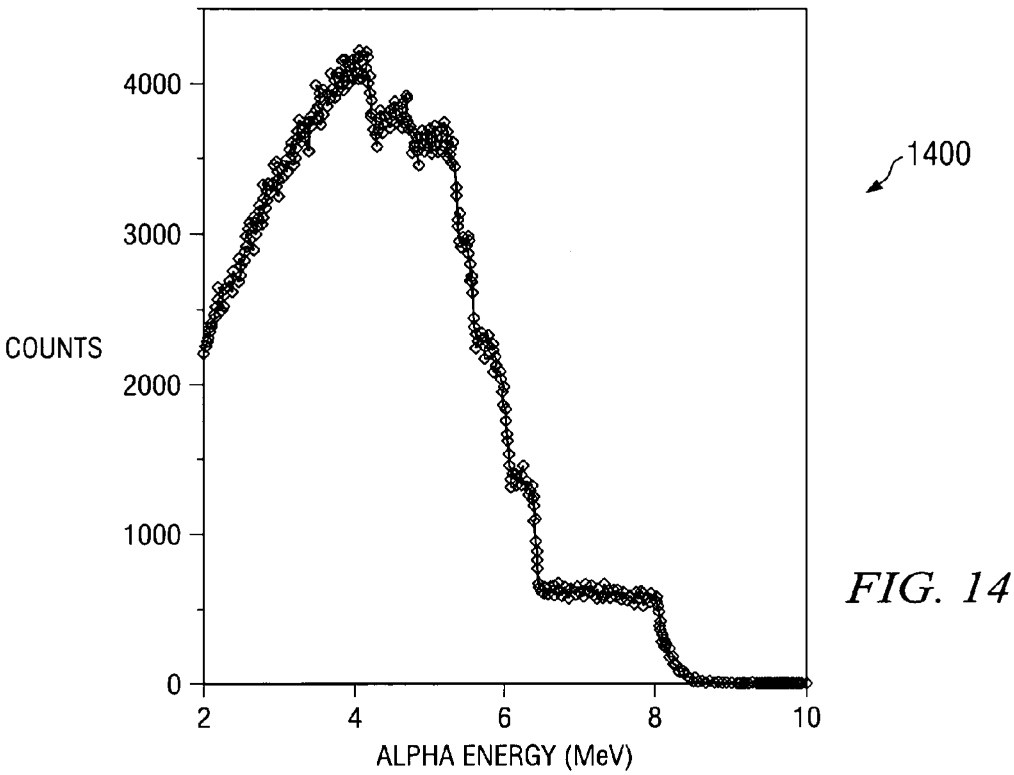
FIG. 14 is a graphical depiction of an exemplary alpha spectrum from a substantially thick sample of Thorium.
Figure 15:
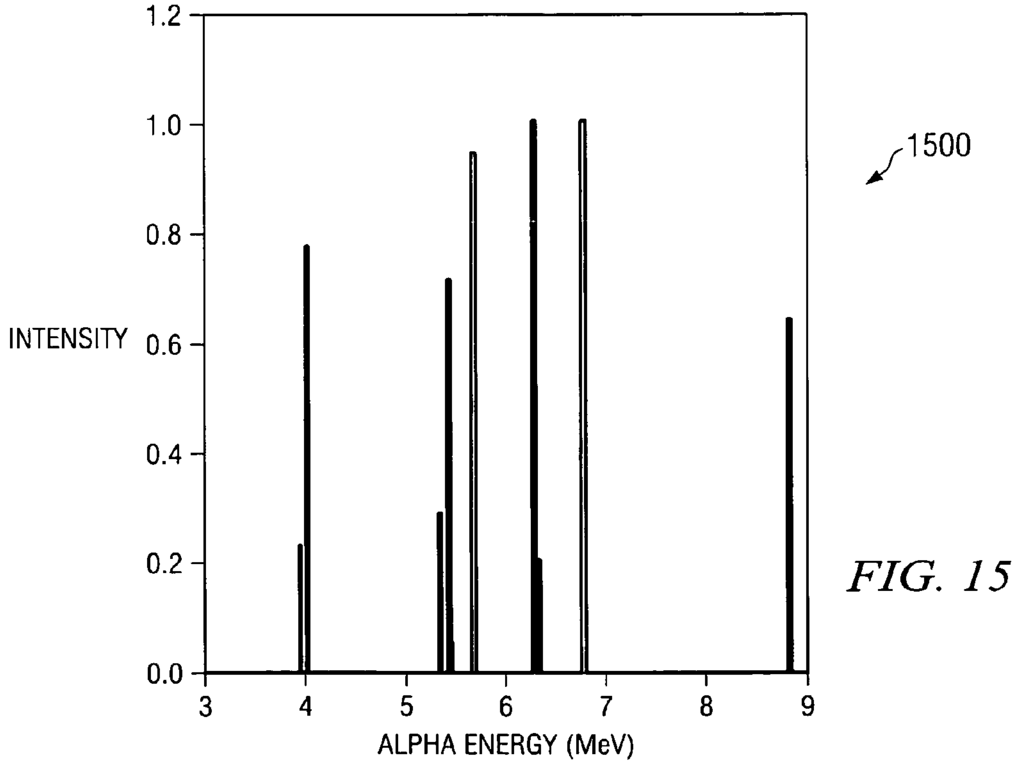
FIG. 15 is a graphical depiction of an exemplary alpha spectrum from a thin film of Thorium.

By way of further example, FIG. 14 graphically depicts an example of an alpha spectrum 1400 from a substantially thick Th-232 sample. It can be seen that the distribution is much smoother than if it would have come from a much thinner sample. FIG. 15 demonstrates just such a situation. In particular, FIG. 15 graphically depicts an example of an alpha spectrum 1500 generated from a thin film of Th-232. The emissions in FIG. 15 are significantly discreet and much less gradual than that presented in FIG. 14.

Use of such mono-energetic producing sources can lead to erroneous soft error rate values, particularly if they are extrapolated directly from a test system. Thus, test data acquired from such sources may need to be manipulated to be useful. The data may have to be transformed, for example, by running it through three dimensional device simulations. Such transformations, however, can be costly, time intensive and may produce results that are inaccurate and/or otherwise unsatisfactory.

Such sources may also have very low activities, which can necessitate long test times (e.g., on the order or days or more). For example, naturally occurring Th232 and U238 both have half lives over ten billion years thus their activities are inherently very low. To the contrary, one or more aspects of the present invention improve the throughput of testing. Soft error rate testing in accordance with one or more aspects of the present invention facilitates quickly and accurately determining a soft error rate from an experiment by utilizing a distributed source (e.g., of alpha particles) to obtain failure rate data and then merely accounting for the increased activity of the source relative to what the device would actually experience in device operation (e.g., as a packaged part) without the need for running time-consuming, expensive and/or potentially inaccurate simulations.

Use of other sources, such as an ion beam, for example, would not provide the broad spectrum of particles, nor the accelerated test time in such a cost effective and efficient manner. In an ion beam, for example, something generally equivalent to a helium nucleus may be accelerated with a high voltage to simulate an alpha particle. However, it may take several million electron volts or more to achieve the necessary acceleration to adequately mimic the characteristics of an alpha particle. Additionally, ion beams do not allow more than one energy level to be selected. Furthermore, since it is a beam, during a single test, multiple angles of incidence are not possible. An ion beam would thus have to be operated at many different accelerator energies and maneuvered to many different orientations to emit ions at different angles as occurs naturally, and this would have to be done for each device being tested. This translates to a significantly increased testing time (e.g., on the order of a hundred or more times longer than that which is contemplated herein). Furthermore ion beam equipment is very specialized, expensive, and requires a large dedicated laboratory space.

One or more aspects of the present invention thus provide a mechanism that facilitates the expeditious and efficient testing of soft error rates, that in turn allows a choice to be made at a design stage regarding which particular element(s) to include in a product design to yield a final product that has a particular failure or soft error rate. Aspects of the present invention provide a metric to designers regarding which element(s) to utilize in producing a final product to achieve desired results (e.g., levels of product reliability). By way of example, designers who have access to ASIC cell libraries, including, for example, $\text{flip-flop}_A$, $\text{flip-flop}_B$, $\text{flip-flop}_C$, etc. can selectively utilize theses elements as is needed to create desired devices. Obtained failure rate data, can also, for example, be utilized in association with simulation and modeling techniques so that an estimate of reliability can be provided for different element types and/or final products. This may be advantageous as it may be impractical to test every different type of logic element and develop failure rate characterization data therefore.

As such, a certain level of product reliability can be built in at the design stage. One or more aspects of the present invention can also facilitate diagnosis of existing product performance. For example, by knowing what elements are included in an existing product, the failure rates of those elements can be obtained from a database of failure rate characterization data to determine or predict what the failure or soft error rate of the existing product should be, and thus whether the actual failure rate of the existing product provides an indication that the product is or is not functioning as intended.

Figure 16:
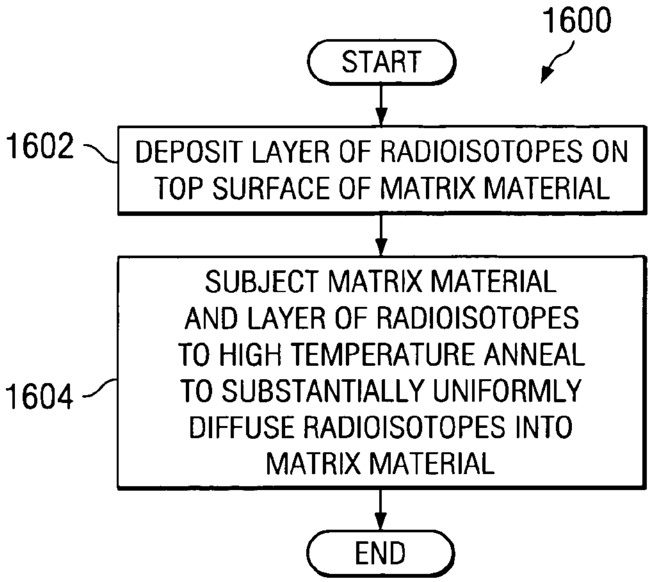
FIG. 16 illustrates a flow diagram of a methodology for fashioning a radiation source suitable for use in a test system adapted to test for soft error or failure rates in one or more semiconductor devices in accordance with one or more aspects of the present invention.
Figure 17:
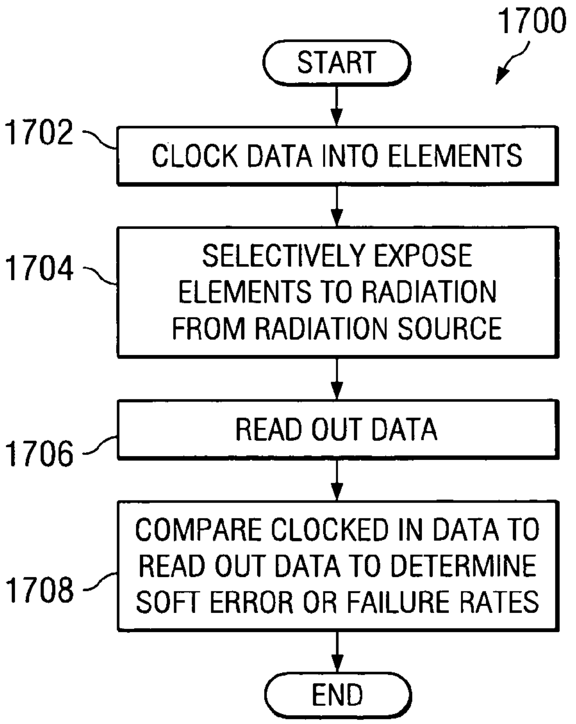
FIG. 17 illustrates a flow diagram of a methodology for utilizing a radiation source such as that disclosed herein in a test system adapted to test for soft error or failure rates in one or more semiconductor devices or elements in accordance with one or more aspects of the present invention.

With reference now to FIGS. 16 and 17, in accordance with one or more aspects of the present invention, methodologies 1600 and 1700 are, respectively, illustrated for fashioning and utilizing a radiation source suitable for use in a test system adapted to test for soft error or failure rates in one or more semiconductor devices, where the devices fail as a result of exposure to radiation from the radiation source, and more particularly where charge sensitive nodes, that have ever decreasing capacitances and voltages as a result of device scaling, are adversely affected by exposure to the radiation. The radiation mimics that to which the device would actually be exposed in practice (e.g., from packaging and/or other materials, such as solder, adjacent to semiconductor circuitry), but is more active (e.g., has a short half life) to increase the rate of failure and expedite the testing process.

Although the methodologies 1600, 1700 are illustrated and described hereinafter as a series of acts or events, it will be appreciated that the present invention is not limited by the illustrated ordering of such acts or events. For example, some acts may occur in different orders and/or concurrently with other acts or events apart from those illustrated and/or described herein, in accordance with one or more aspects of the present invention. In addition, not all illustrated steps may be required to implement a methodology in accordance with the present invention. Furthermore, any methodologies according to the present invention may be implemented, to varying degrees, in association with the formation and/or processing of structures that may or may not be illustrated and described herein.

Methodology 1600 begins at 1602 wherein a layer of radioisotopes is deposited onto a top surface of an encapsulating matrix material. The radioisotopic materials utilized are chosen such that their emission energies are similar to, but more active (e.g., have a shorter half life) than that of corruptive alpha or other particles associated with the packaging environment that the die/circuitry will experience in operation. The elements that are exposed to the radiation thus get an increased dosage of the radiation to exacerbate soft error rates and expedite the testing process.

The matrix can include any of a number of suitable materials, alone or in combination, such as metal, semiconductor and/or ceramic matrix materials comprising, respectively, platinum, stainless steel, silicon and/or alumina, for example. The radioisotropic materials can similarly include any one or more isotopes that have alpha emissions similar to that of impurities within packaging and/or other materials which give off radiation in real devices. By way of example, the radioisotropic materials can include thorium (e.g., Th-228) and/or americium (e.g., Am-241) to give off radiation over a broad range of energies (e.g., from about 0–10 MeV) to simulate, respectively, alpha emissions from mold compounds used to encapsulate many integrated circuits (ICs) and solder bumps.

The methodology 1600 then advances to 1604, and ends thereafter. At 1604, the matrix material and layer of radioisotopes are subjected to a high temperature anneal to substantially uniformly distribute the radioisotopes within the matrix material. The anneal process causes some of the radioisotopes to move from the top surface of the matrix material down toward a bottom surface of the matrix material in a generally graduated fashion. The radioisotopic materials serve as emission sites and are operative to emit radiation particles that mimic radiation that semiconductor devices would actually encounter in practice (e.g., due to packaging and/or other materials such as solder balls adjacent to semiconductor circuitry). The radiation particles, in operation, exit the matrix material through the bottom surface, for example, and the substantially uniform distribution of radioisotopes within the matrix material allows the radiation particles to encounter test element(s) at a wide variety of different angles and with a variety of different energies similar to what would actually be encountered in practice. The different energy levels are achieved, at least in part, because the particles lose energy as they travel through the matrix. In particular, the more material the particles have to traverse to escape the matrix, the less energy they have when they leave the matrix.

It will be appreciated, however, that the distribution of the radioisotopic materials within the matrix can be accomplished in any of a number of different fashions, including, for example, thermal diffusion, implantation and/or mixing of the isotope with a liquid or powdered matrix which is then solidified by curing, annealing and/or some other process.

When implemented within a test system, the radiation source is utilized to selectively expose one or more test element(s) to radiation. More particularly, the radiation source is controllable so that the element(s) can be selectively exposed to the radiation (e.g., for a particular period of time). The test element(s) may comprise a plurality of elements of a particular type of element to be tested (e.g., flip-flop$_A$, flip-flop$_B$, flip-flop$_C$, etc.), which may be connected in series as a string of elements (e.g., on the order of a thousand or more elements) to magnify the occurrence of soft errors and thereby accelerate the test time. Such a plurality of elements of a particular element type to be tested can, for example, be strung together as synchronously clocked serial first in, first out (FIFO) buffers or chains, where the output of one element feeds into or acts as an input to a subsequent element in the chain.

Turning to FIG. 17, a methodology 1700 is disclosed for utilizing a radiation source, such as that described above, in a test system adapted to test for soft error or failure rates in one or more semiconductor devices or elements. The methodology 1700 begins at 1702 wherein data is clocked into a string of the devices or elements. A data source (e.g., of all 1's, all 0's, alternating 1's and 0's or any other known pattern of 1's and 0's) can, for example, be coupled to the string of elements and cycled into the elements by a clock signal which is also coupled to the string of elements. By way of example, should all 1's be fed into the string, a first 1 is fed in and clocked so that it goes into a first element in the string. A second 1 is then fed in and clocked so that the first 1 is advanced to a second element and the second 1 fills the first element. The process continues until the respective elements in the string contain 1's. At 1704, the radiation source is then operatively associated with the string so as to selectively expose the one or more test element(s) to the radiation.

At 1706 data is read out of the elements as the data passes through the length of elements and exits out through the last element in the chain. At 1708 data input into the chain is compared to data read out of the chain to determine a soft error rate. Variations between the known clocked in pattern and the output data are indicative of failures or soft errors. The methodology then ends after 1708.

It will be appreciated that the ordering of the acts is not absolute and/or to be construed in a limiting sense. For example, when the radiation source is implemented with a test system the methodology can be carried out in static as well as dynamic modes. In a static mode, the respective elements can be filled with data (e.g., all 1's) prior to being exposed to radiation from the radiation source. The radiation is then applied for a particular period of time and then taken away from the string of elements before the data is read out from the elements. The known clocked in data stream is then compared to the output data to see if any soft errors have occurred. In a dynamic mode, data of a known pattern (e.g., all 1's, all 0's, alternating 1's and 0's) can be quickly and continuously written to the element strings while the elements are exposed to radiation from the radiation source, and data output from the strings is constantly read out and compared to input data while the elements remain exposed to the radiation.

Additionally, one or more acts of the methodology can be carried out concurrently to develop failure rate data for more than one type of element operating under the same (or different) test conditions. In such a scenario, an input source and a clock would likely be connected to respective chains of different type of elements to be tested. In this manner, data of a known pattern can be clocked into each of the respective chains and data output from the chains can be compared to this input data to see if any failures or soft errors have occurred in any of the respective chains of elements. In one example, the lengths of the chains would be the same for each of the types of elements to develop coincident test data. The lengths of the chains should also be long enough to develop a sufficient amount of test data in a reasonable amount of time. For example, chain lengths on the order of a thousand or more elements per chain should allow test data to be developed within several hours. As scaling continues and sensitivity increases accordingly, the lengths of chains can be reduced, which may allow more types of elements to be tested simultaneously as more chains can be squeezed onto a single test chip.

Failure rates in a particular time frame can then be obtained for the respective types of elements being tested since the radiation exposure time, type and intensity are known, and the number of elements that fail during this exposure time period can be been determined. This can be utilized to compute what an actual failure rate would be for the respective elements when the elements are implemented in the field. It will be appreciated that the foregoing is not intended to only pertain to special logic structure, but also has application to more conventional test structures (e.g., for DRAM/SRAM testing).

Although the invention has been shown and described with respect to one or more implementations, equivalent alterations and/or modifications may be evident based upon a reading and understanding of this specification and the annexed drawings. The invention includes all such modifications and alterations and is limited only by the scope of the following claims. In particular regard to the various functions performed by the above described components (assemblies, devices, circuits, etc.), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary implementations of the invention. In addition, while a particular feature of the invention may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A test radiation source suitable for use in a test system operative to test for soft error or failure rates in one or more semiconductor devices, wherein test radiation from the test radiation source mimics radiation that the devices would actually encounter in device operation, the source comprising:

a matrix material; and one or more radioisotopes substantially uniformly distributed within the matrix material, wherein the radioisotopes act as emission sites and emit the test radiation.

2. The source of claim 1, wherein the one or more radioisotopes have a relatively short half life such that the devices experience an increased exposure to the test radiation as compared to the amount of the radiation that the devices would actually receive in device operation, and such that the devices exhibit an enhanced soft error rate so that testing time is thereby reduced.

3. The source of claim 1, wherein the matrix material comprises at least one of platinum, stainless steel, silicon and alumina.

4. The source of claim 1, wherein the one or more radioisotopes comprise at least one of uranium, thorium and americium.

5. The source of claim 4, wherein the one or more radioisotopes comprise at least one of Th-228 and Am-241.

6. The source of claim 1, wherein the one or more radioisotopes mimic radiation from at least one of solder, plastic packaging, ceramic packaging, quartz, epoxy, alumina, glass, polyamides, metal filled polymers, ceramic filled polymers, diamond filled polymers, silver glass, copper, aluminum, polyurethane, thermal grease and thermoplastic.

7. The source of claim 1, wherein the test radiation is emitted from a bottom surface of the matrix material and wherein the substantially uniform distribution of the radioisotopes allows the radiation to encounter the one or more semiconductor devices being tested at a variety of angles and with a variety of different energies similar to what would actually be encountered in device operation.

* * * * *